United States Patent
Pacholski et al.

(10) Patent No.: US 9,132,445 B2
(45) Date of Patent: Sep. 15, 2015

(54) HIGHLY ORDERED ARRAYS OF NANOHOLES IN METALLIC FILMS AND METHODS FOR PRODUCING THE SAME

(75) Inventors: Claudia Pacholski, Stuttgart (DE); Stefan B. Quint, Stuttgart (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 821 days.

(21) Appl. No.: 13/203,985

(22) PCT Filed: Mar. 5, 2009

(86) PCT No.: PCT/EP2009/001574
§ 371 (c)(1),
(2), (4) Date: Sep. 30, 2011

(87) PCT Pub. No.: WO2010/099805
PCT Pub. Date: Sep. 10, 2010

(65) Prior Publication Data
US 2012/0028029 A1 Feb. 2, 2012

(51) Int. Cl.
C23C 14/04 (2006.01)
C23C 18/06 (2006.01)
B05D 1/00 (2006.01)
B05D 1/32 (2006.01)
B82Y 30/00 (2011.01)
B82Y 40/00 (2011.01)
C23C 18/16 (2006.01)
C23C 18/18 (2006.01)
C23C 18/44 (2006.01)
G01N 21/552 (2014.01)

(52) U.S. Cl.
CPC ............... B05D 1/005 (2013.01); B05D 1/322 (2013.01); B82Y 30/00 (2013.01); B82Y 40/00 (2013.01); C23C 18/1605 (2013.01); C23C 18/1689 (2013.01); C23C 18/1692 (2013.01); C23C 18/1882 (2013.01); C23C 18/44 (2013.01); G01N 21/554 (2013.01); Y10T 428/249978 (2015.04)

(58) Field of Classification Search
CPC ........ B05D 3/067; B82Y 15/00; B82Y 40/00; B82Y 30/00; B32B 2255/205; B01J 23/52; B01J 35/0013
USPC ................. 427/270; 428/315.5; 977/840, 700
See application file for complete search history.

(56) References Cited

FOREIGN PATENT DOCUMENTS

CN 1827854 A 6/2006
WO 2006131400 A1 12/2006

OTHER PUBLICATIONS

Murray et al., "Transition from localized surface plasmon resonance to extended surface plasmon-polariton as metallic nanoparticles merge to form a periodic hole array", Physical Review B, vol. 69, pp. 165407-pp. 1-7 (Apr. 2004).*
Hulteen et al.,"Nanosphere Lithography: Size-Tunable Silver Nanoparticle and Surface Cluster Arrays", Journal of Phys. Chemistry, B 1999, 103, pp. 3854-3863.*
Van Duyne et al., "Nanosphere Lithography: A Materials General Fabrication Process for Periodic Particle Array Surfaces", American Vacuum Society, 1995, pp. 1553-1558.*
Haynes et al., "Nanosphere Lithography: A Versatile Nanofabrication Tool for Studies of Size-Dependent Nanoparticle Optics", Journal of Phys. Chemistry B, 2001, 105, pp. 5599-5611.*
Li et al. "Silver Hierarchical Bowl-Like Array: Synthesis, Superhydrophobicity, and Optical Properties", Langmuir, 2007, 9802-9807.*
Jiang et al., "Two-Dimensional Nonclose-Packed Colloidal Crystal Formed by Spincoating", Applied Physics Letters 89, Jul. 6, 2006.*
Wijnhoven et al., "Electrochemical Assembly of Ordered Macropores in Gold", Advanced Materials, 2000, 12, No. 12, pp. 888-890.*
Tsuji et al., "Colored Thin Films Prepared From Hydrogel Microspheres", Langmuir 2005, 21, 8439-8442.*
Wood, "Colloidal Lithography and Current Fabrication Techniques Producing Inplane Nanotopography for Biological Applications", Journal of the Royal Scociety Interface, Feb. 22, 2007, pp. 1-20.*
Dong et al., "Fabrication of Two-Dimensional Arrays of Micron-Sized Gold Rings Based on Preferential Nucleation at Reentrant Sites", IOP Science, vol. 25, No. 8, 2008, pp. 2957-2959.*
DeLeebeck et al., "On-Chip Surface-Based Detection with Nanohole Arrays", Analytical Chemistry, vol. 79, No. 11, pp. 4094-4100 (2007).
Guan et al., "Fabrication of patterned gold microscope by selective electroless plating", Applied Surface Science, vol. 240, pp. 24-27 (2005).
Murray et al., "Transition from localized surface plasmon resonance to extended surface plasmon-polariton as metallic nanoparticles merge to form a periodic hole array", Physical Review B, vol. 69, pp. 165407-1-165407-7 (2004).

(Continued)

*Primary Examiner* — William Phillip Fletcher, III
(74) *Attorney, Agent, or Firm* — Caesar Rivise, PC

(57) ABSTRACT

The present invention relates to highly ordered arrays of nanoholes in metallic films and to an improved method for producing the same. The method according to the invention for producing an highly ordered array of nanoholes in metallic films on a substrate comprises the following steps: a) providing microspheres comprising poly-N-isopropylamide (polyNIPAM), the microspheres being selected from pure poly-N-isopropyl-amide (polyNIPAM) hydrogel microspheres and polymeric or inorganic beads carrying poly-N-isopropylamide (polyNIPAM) hydrogel chains, b) coating an aqueous dispersion of said microspheres onto a substrate and drying the dispersion, which results in a non-close packed ordered array of the microspheres, c) generating a metallic film on the substrate, d) removing the microspheres from the surface of the substrate which results in an ordered array of nanoholes on the substrate, and e) optionally increasing the thickness of the metallic film by selective electroless plating.

10 Claims, 5 Drawing Sheets

(56) References Cited

OTHER PUBLICATIONS

Pelton et al., "Preparation of Aqueous Latices with N-Isopropylacrylamide", Colloids and Surfaces, vol. 20, pp. 247-256 (1986).

Rybczynski et al., "Large-scale, 2D arrays of magnetic nanoparticles", Colloids and Surfaces A: Physicochem. Eng. Aspects, vol. 219, pp. 1-6 (2003).

Sharpe et al., "Gold Nanohole Array Substrates as Immunobiosensors", Anal. Chem., vol. 80, pp. 2244-2249 (2008).

Tsuji et al., "Colored Thin Films Prepared from Hydrogel Microspheres", Langmuir, vol. 21, pp. 8439-8442 (2005).

Tsuji et al., Self-Assembly of Poly(N-isopropylacrylamide)—Carrying Microspheres into Two-Dimensional Colloidal Arrays, Langmuir, vol. 21, pp. 2434-2437 (2005).

Xia et al., "Monodispersed Colloidal Spheres: Old Materials with New Applications", Adv. Mater., vol. 12, No. 10, pp. 693-713, (2000).

Yang et al., "Nanomachining by Colloidal Lithography", Small, vol. 2, No. 4, pp. 458-475 (2006).

International Search Report for PCT/EP2009/001574 dated Jan. 4, 2010.

Du et al., "Localized surface plasmons, surface plasmon polaritons, and their coupling in 2D metallic array for SERS", Optics Express, vol. 18, No. 3, pp. 1959-1965 (2010).

* cited by examiner

HIGHLY ORDERED ARRAYS OF NANOHOLES IN METALLIC FILMS AND METHODS FOR PRODUCING THE SAME

BACKGROUND

Nanostructured free-electron metals gained a lot of attention due to their interesting optical properties that are based on resonant excitation of surface plasmons (SP). SPs are waves of oscillating surface charge density traveling along the metal surface. The manipulation of SPs properties by tailoring the geometric parameters of the nanostruture is a promising approach for the development of plasmonic-based applications such as device fabrication, imaging technologies, and information processing. Sub-wavelength nanohole arrays in thin gold films show an especially interesting optical phenomenon called "extraordinary optical transmission" (EOT). These nanostructures are more transparent at certain wavelengths than expected by the classical aperture theory and can be used for enhanced spectroscopy as well as chemical sensing. Sensors based on this technology could offer several advantages such as higher spatial resolution, greater reproducibility, and more convenient experimental geometries.

In recent years, colloidal nanolithography has made considerable progress (Xia et al., Adv. Mater. 2000, 693-713; Yang et al., Small 2007, 2, 458-475) and has also been used for producing nanostructures showing an EOT effect. In particular, Murray et al. (Physical Review B 69, 165407-1-165407-7 (2004) used an ordered monolayer of polystyrene nanospheres as a deposition mask through which silver was deposited by thermal evaporation. By reactive ion etching of the nanospheres in an oxygen plasma prior to silver deposition, arrays consisting of silver particles of increasing size were produced which—with increasing etching time—gradually merged into a continuous metal film perforated by a periodic nanohole array in a silver film. This method requires a rather expensive equipment and is laborious due to the plasma etching step, which has to be optimized for every plasma machine again. Moreover, the surface of the polystyrene spheres is increasingly frayed out during plasma exposure leading to a loss of the spherical shape of the polymer mask. The surface roughness of the polymer spheres increases proportionally to the process duration which has a direct effect on the quality of the pore rims of the metal layer deposited thereafter. In view of the drawbacks of this method as well as that of other nanolithography techniques of the art, periodic arrays of nanoholes in opaque metal films are usually fabricated by focused ion beam, electron beam lithography, and photolithography until now (De Leebeeck et al., Anal. Chem. 2007, 79, 4094-4100; Sharpe et al., Anal. Chem. 2008, 80, 2244-2249). These techniques are limited by either low resolution (photolithography) or low throughput (e-beam lithography, focused ion beam lithography). They are time-consuming, expensive, and provide only small nanostructured areas.

Thus, an object of the present invention is to provide improved methods for producing highly ordered arrays of nanoholes in metallic films on a substrate which are fast, cost-efficient and simple to perform without the need of expensive equipment, for example in any standard chemical laboratory. A further object is to provide large and highly ordered arrays of nanoholes in metallic films on a substrate, with the size and lattice constant of the nanoholes being easily adjustable over a broad range.

Said objects are achieved by providing a novel method involving colloidal nanolithography for producing highly ordered arrays of nanoholes in metallic films on a substrate according to the present invention and by providing the highly ordered array of nanoholes according to the present invention.

DESCRIPTION OF THE INVENTION

The method according to the invention for producing an highly ordered array of nanoholes in metallic films on a substrate comprises the following steps:
a) providing microspheres comprising poly-N-isopropylamide (polyNIPAM), the microspheres being selected from pure poly-N-isopropyl-amide (polyNIPAM) hydrogel microspheres and polymeric or inorganic beads carrying poly-N-isopropylamide (polyNIPAM) hydrogel chains,
b) coating an aqueous dispersion of said microspheres onto a substrate and drying the dispersion, which results in a non-close packed ordered array of the microspheres,
c) generating a metallic film on the substrate,
d) removing the microspheres from the surface of the substrate which results in an ordered array of nanoholes on the substrate, and
e) optionally increasing the thickness of the metallic film by selective electroless plating.

In a preferred embodiment, the method of the invention further comprises
f) incubation of the substrate obtained after step d) or step e) in a vacuum oven.

Surprisingly, it has been found that poly-N-isopropylamide (polyNIPAM) microspheres can be advantageously used to provide a deposition mask for metallic films on a substrate which mask can be both produced and eliminated in a fast and simple manner and gives rise to large and highly ordered arrays of nanoholes in a metallic film.

It has been known in the prior art that self-assembling poly-N-isopropylamide (polyNIPAM) microspheres can be used to produce two-dimensional colloidal arrays, with the superlattice structure of these colloids being controllable by designing the particle structure (Tsuji and Kawaguchi, Langmuir 2005, 21, 2434-2437). However, the authors of this publication did neither disclose nor suggest the use of said polyNIPAM microspheres for preparing a lithographic mask.

Moreover, Tsuji and Kawaguchi prepared the colloidal arrays by dropping an aqueous PNIPAM microgel dispersion onto various substrates and air-drying. Experiments of the present inventors revealed that these conditions resulted in an uneven distribution of the deposited microgel particles and both the near-range and the long-range order of the colloidal arrays obtained by this method was not satisfying for the use as a lithographic mask (see Example 2 as well as FIGS. 7A and 7B below). The uneven distribution of the deposited microgel particles is based on the increasing concentration of particles in the dispersion upon drying. Therefore the two-dimensional array shows a lot of defects and the EOT effect is significantly decreased.

In an effort to develop a suitable method for producing a highly ordered array of nanoholes in metallic films on a substrate, the present inventors conducted an extensive series of experiments, as a result of which several relevant parameters were identified and a number of especially advantageous and effective steps for use in such a method were developed.

The first step a) of the method according to the invention is not critical and the polyNiPAM microspheres which may be pure poly-N-isopropyl-amide (polyNIPAM) hydrogel microspheres or polymeric or inorganic beads carrying poly-N-isopropylamide (polyNIPAM) hydrogel chains can be synthesized according to published methods (e.g. Pelton and Chibante, Colloids and Surfaces 1986, 20, 247-256). In this step, polyNIPAM hydrogel chains with varying length and hydrogel particles with different diameters and swelling ratios can be prepared and these parameters can be used to adjust the lattice constant and hole diameter of the periodic arrays formed subsequently (microgel particle sizes: 200-1000 nm). In the case of hydrogel chain carrying polymeric or inorganic beads, the beads may be of any material which can be functionalized with polyNIPAM chains. Some non-limiting examples are polystyrene, polymethylmethacrylate, latex, $SiO_2$, $TiO_2$, $ZrO_2$, $CeO_2$ etc.

These microspheres self-assemble into a two-dimensional superlattice when their dilute suspension is dried on surfaces. The array formation is mainly driven by capillary forces between the microspheres during water evaporation. In the case of hydrogel-chain carrying microspheres coalescence is prevented by the hydrogel coating. This hydrogel layer collapses upon drying leading to the formation of non-closely packed arrays.

The coating of the polyNIPAM dispersion onto the substrate in step b) may be effected in any manner known in the art which results in highly ordered arrays of the PNIPAM particles or microspheres. In a preferred embodiment of the invention, the coating of the PNIPAM dispersion onto the substrate in step b) is effected by spin-coating. In an even more preferred embodiment, the spin-coating comprises at least two different spinning operations with different speeds. In particular, it has been found that a first spinning operation with a relatively low speed, preferably in the range from 100 rpm to 1000 rpm, followed by a second spinning at a higher speed, preferably in the range of from 1000 rpm to 10000 rpm, results in colloidal arrays with a significantly higher degree of near-range and far-range order in comparison to air-dried samples.

It has also been observed that the addition of a lower alkyl alcohol to the dispersion applied on the substrate before the spinning operations is very advantageous and greatly enhances the formation of highly ordered polyNIPAM microspheres. Preferably, the lower alkyl alcohol is selected from the group consisting of methanol, ethanol and propanol and most preferably the alcohol is ethanol.

The substrate to be coated may be any substrate capable to be coated with the polyNIPAM microspheres and the metallic film. Some non-limiting examples are glass, silica, polystyrene, with glass especially preferred.

The metallic film applied to the surface in step c) may be any metallic film suitable to be deposited on the substrate and capable to show the "EOT" effect if an highly ordered array of nanoholes is provided therein. Preferably the metallic film is a noble metal film, in particular a gold or silver film. The metal film should have a final thickness in the range of from 50 to 500 nm, preferably 100 to 250, more preferably around 150 nm, in order to provide nanoholes having a depth of this order of magnitude.

Said metallic film may be generated by any suitable method for depositing a metal film on the respective substrate. Preferably, the film is generated by either thermal evaporation or by functionalizing the surface areas not covered by microspheres with a compound which enables or favours a selective deposition of the metal on the substrate by electroless plating.

In a specific embodiment of the invention, the metal is gold and the compound used for functionalizing the surface is an aminosilane, for example 3-aminopropyl-triethoxysilane. Other suitable compounds for this purpose will be recognized by the skilled artisan.

The selective deposition of the metal induced by a functionalized surface may be advantageous over thermal evaporation, since in the latter method care has to be taken that the microspheres are not completely buried in the metal film which renders the microspheres difficult or impossible to remove by conventional methods such as ultrasonication.

Typically, a metal layer having a thickness of approximately 100-200 nm is produced in step c) and then the colloidal mask is removed.

In a preferred embodiment of the invention, the method used for removing the microspheres in step d) involves immerging the substrate in a wash solution, e.g. a mixture of water and an organic solvent, such as MeOH, and subjecting to ultrasonication for a suitable time period, e.g. for 30 minutes.

In another preferred embodiment of the invention, the method used for removing the microspheres in step d) involves a flame annealing step at a temperature in the range of from appr. 250 to 2000° C., typically from 400 to 1500° C., more specifically from 400 to 1000° C., which pyrolyzes and removes the polyNIPAM microspheres but does not negatively affect the metallic film. This method is particularly advantageous, since it is very fast and easy to perform and also allows to reduce the internal and external roughness of the metal film.

Typically, in step e) the thickness of the metal layer is increased by selective electroless plating according to known methods (e.g. as disclosed in Guan et al., Appl. Surf. Sci. 2005, 240, 24-27) to a desired value, e.g. in a range of 100-300 nm, preferably 120-250 nm, more preferably around 150 nm.

In a preferred embodiment, the method of the invention further comprises a step f) wherein the substrate obtained after step d) or step e) is incubated in a vacuum oven. This step results in an enhancement of the EOT effect exhibited by the nanohole array produced as outlined above.

Typically, in step f) the nanohole arrays are incubated at 300-500° C., e.g. at about 400° C., and $10^{-2}$-$10^{-4}$ torr, e.g. about $10^{-3}$ torr, for at least 10 h, preferably at least 20 h, e.g. 20-30 h. However, as recognized by the skilled artisan, the incubation conditions may be varied as appropriate for different substrates and metallic films and suitable conditions can be readily determined by routine experiments.

A closely related aspect of the present invention are the highly ordered arrays of nanoholes obtainable with the above method. These highly ordered arrays are considerably larger than those produced with prior art methods of colloidal nanolithography and can even be present in a surface area in the order of square centimeters. Furthermore, the arrays are characterized by the size and form of the nanoholes which directly correspond (as a negative) to the size and form of the polyNIPAM microspheres used as a lithographic mask to produce said array of nanoholes. In contrast to holes produced by etching methods or ion/electron beam treatments, the edges of the nanoholes produced by the inventive method are rounded.

The highly ordered arrays of nanoholes according to the invention are of interest for a wide variety of applications where the EOT effect is used, in particular in the fields of chemical and biochemical sensing, imaging technology, information processing and enhanced spectroscopy.

Thus, a further aspect of the invention relates to a device, in particular an optic device, spectroscopic device or sensor device, comprising said highly ordered arrays.

The present invention is illustrated in more detail in the following non-limiting examples.

EXAMPLE 1

Preparation of a Highly Ordered Nanohole Array in Gold Films

In a specific embodiment of the present invention, nanohole arrays in gold films on a glass substrate were produced using two-dimensional colloidal arrays of polyNIPAM microspheres as a nanolithographic mask.

As substrates 2×2 cm hydrophilic microscope cover glass plates (Roth, Germany) were used. The glass plates were cleaned in Piranha solution (3:1 concentrated $H_2SO_4$/30% $H_2O_2$) for 1.5 h followed by sonication in an ultrasonic bath and abundant washing with ultra pure water. The cleaned plates were kept under deionized water from 1 to 24 h and were blow dried just before the experiment.

As an initial step, poly-N-isopropylacrylamide (polyNIPAM) microspheres were synthesized according to published methods (Yang et al., Small 2007, 2, 458-47).

The experiments were carried out with different suspensions of polyNIPAM microspheres. The concentrations along with the poly(NIPAM) array specifications are shown in the tables below:

| Identifier | Center-to-center distance [nm] | Poly(NIPAM)disc diameter (dry) [nm] |
|---|---|---|
| R13 | 494 | 312 |
| SP13 | 1200 | 860 |
| SP73 | 655 | 395 |

| Identifier | Concentration [g/l] | Used dilution after filtration |
|---|---|---|
| R13 | 15.71 ± 0.04 | 1:300 |
| SP13 | 19.6 ± 0.4 | 1:50 |
| SP73 | 8.6 ± 0.2 | 1:100 |

Prior to use, the microsphere suspensions were purified by filtration using Acrodisc 25 mm Syringe Filters with Versapor membranes. The pore diameter of the used membranes was 1.2 μm in case of SP13 and 0.8 μm for the other microspheres. After filtration the suspensions were diluted with water as specified in the table above.

Figure 1:
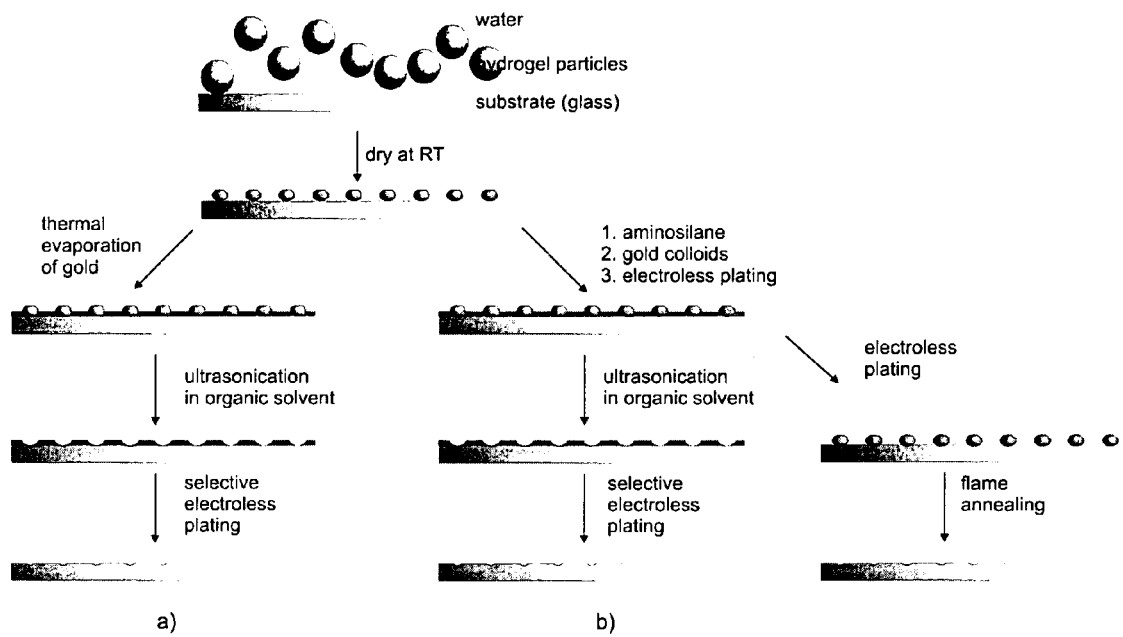
FIG. 1. Flow chart of the principal steps to produce nanoholes in gold films according to the invention.

FIG. 1 illustrates the principal steps involved in the fabrication process. In the first step a dilute dispersion of polyNIPAM microspheres is dried on a glass cover slip (2×2 cm, treated as indicated above) under addition of EtOH in a spin coating system.

Typically, cleaned glass substrates were mounted in the spin coater (e.g. a Laurell WS-400A-6NPP Lite spin coater (Laurell Technologies Corporation, North Wales) and a 40 μl droplet of a diluted polyNIPAM microsphere suspension was placed in the center of the substrate. Subsequently 20 μl of ethanol was added on top of the droplet. Upon this, the droplet retracted and then spread thus wetting the complete substrate. The latter step was repeated two more times. We observed in our experiments that this procedure dramatically enhances the formation of highly ordered arrays of polyNIPAM microspheres. Subsequently the sample was rotated for 6 min at 500 rpm followed by 1 min at 6000 rpm using an acceleration of 100 rpm/s in both cases.

Upon this, the microspheres self-assemble into a highly ordered two-dimensional hexagonal lattice. In principle, the array formation is driven by attractive capillary forces between the microspheres and their convective transport toward the ordered region during water evaporation. However, this effect has been established for stationary systems free of organic solvents. The system used in the present invention and in particular the presence of ethanol might involve further effects not described before. PolyNIPAM exhibits the interesting property that it can undergo a reversible phase transition between a swollen and a shrunken state. Due to this, the close packed swollen polyNIPAM microspheres shrink upon drying and form a non-close packed hexagonal array.

In the second step a ~150 nm thick gold film (as it was determined by AFM measurements) is deposited. Since the deposited gold film should only fill the space between the microspheres, common thin film deposition techniques such as evaporation or sputtering are disadvantageous in that the deposited film would cover the whole sample surface including the colloidal mask. Therefore, the gold film is preferably generated by electroless plating.

To do this, the glass surface is functionalized first with 3-aminopropyl-triethoxysilane by vapor deposition. Previously spin coated samples were encased in a standard exsiccator together with a small dish containing 30 μl of 3-aminopropyltriethoxysilane. The exsiccator was evacuated until a pressure of 0.3 mbar was reached. The samples were kept under these conditions for 30 min to allow a dense silanization of the glass surface. Afterwards the samples were incubated for 1 h in a drying oven at 80° C.

Afterwards the sample is incubated for 30 min at room temperature with an aqueous solution of gold colloids (15 nm colloids, standard deviation: 10%) which had been prepared by citrate reducing according to a method of the prior art. Subsequently the samples were rinsed with ultra pure water. To lift off the polyNIPAM microspheres as well as to remove non-specific bound gold colloids, the samples were immersed in a wash solution (1:20, H2O:MeOH) and sonicated for 30 min.

In the third and final step the gold colloids are grown to form a homogenous gold-layer by selective electroless plating. Electroless deposition of gold was carried out in small glass beakers on a vibrating table. The used glassware was cleaned by aqua regia before usage. Samples decorated with gold colloids were immersed in an aqueous solution of 0.4 mM hydroxylamine hydrochloride and 0.5% $HAuCl_4.3H_2O$.

The solution was agitated on a vibrating table to ensure the formation of a homogenous gold film. After 1 h the samples were rinsed with water and blown dried under a nitrogen stream.

Alternatively the polyNIPAM beads were removed by flame annealing in a 80% butane/20% propane flame (400-1500° C.) after electroless deposition of a ~150 nm thick gold film. Thus, the polyNIPAM microspheres were pyrolyzed and the gold surface was flattened.

Figure 4:
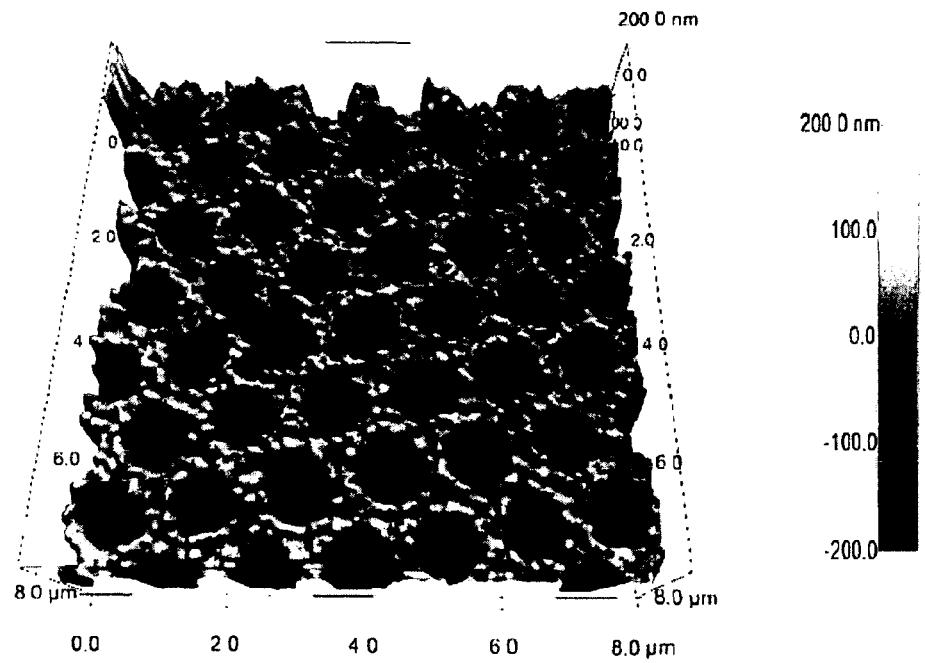
FIG. 4. AFM image of a hole array produced according to the invention.
Figure 5A:
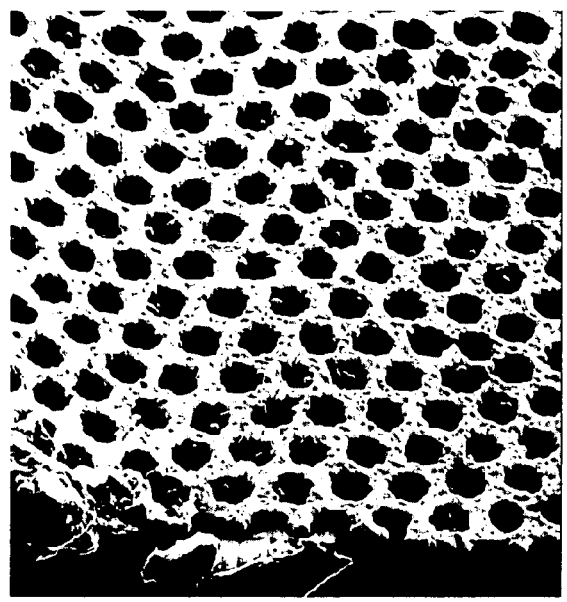
FIG. 5. SEM micrographs of the nanohole structure;
(A) view at 45° angel of inclination; (B) view at 90° angel of inclination.
Figure 5B:

The thickness of the gold layer was determined by AFM measurements. The results are shown below and FIG. 4 shows a sample image of the hole array produced on the basis of SP13:

| Identifier | Layer thickness [nm] |
|---|---|
| R13 | 108 ± 20 |
| SP13 | 162 ± 26 |
| SP73 | 146 ± 11 |

Figure 2:
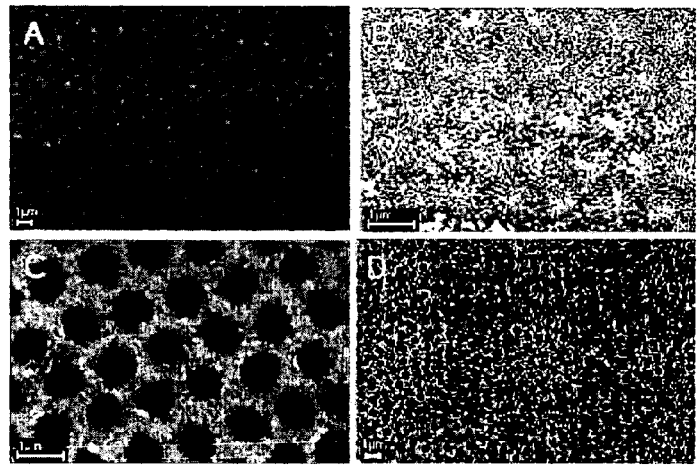
FIG. 2. SEM images of the principal fabrication steps. (A) Ordered array of polyNIPAM beads (dark circles) after spin-coating; (B) Sample surface after incubation with gold colloids (bright spots); (C) Sample surface after removal of the polyNIPAM beads by ultrasonication; (D) Highly ordered array of nanoholes in a homogenous gold film after selective electroless deposition of gold.

In FIG. 2 scanning electron microscope (SEM) images of the fabrication steps are shown. FIG. 2A shows the glass surface after spin coating with polyNIPAM microspheres. As it is apparent, the procedure led to the formation of a highly ordered hexagonal array of microspheres. FIG. 2B displays a SEM image of the surface decorated with gold colloids. The obtained nanostructure after electroless deposition and flame annealing is shown in FIG. 2C. The hole diameter and the lattice constant of the array is correlated to the diameter of the swollen and shrunken polyNIPAM microspheres (e.g. Pelton and Chibante, Colloids and Surfaces 1986, 20, 247-256 and Tsuji and Kawaguchi, Langmuir 2005, 21, 2434-2437). In the presented case spheres were used, which should exhibit a diameter of 1200 nm in the swollen and a diameter of 860 nm in the shrunken state.

EXAMPLE 2

Characterization of Hole Arrays in Gold Films

Figure 3:
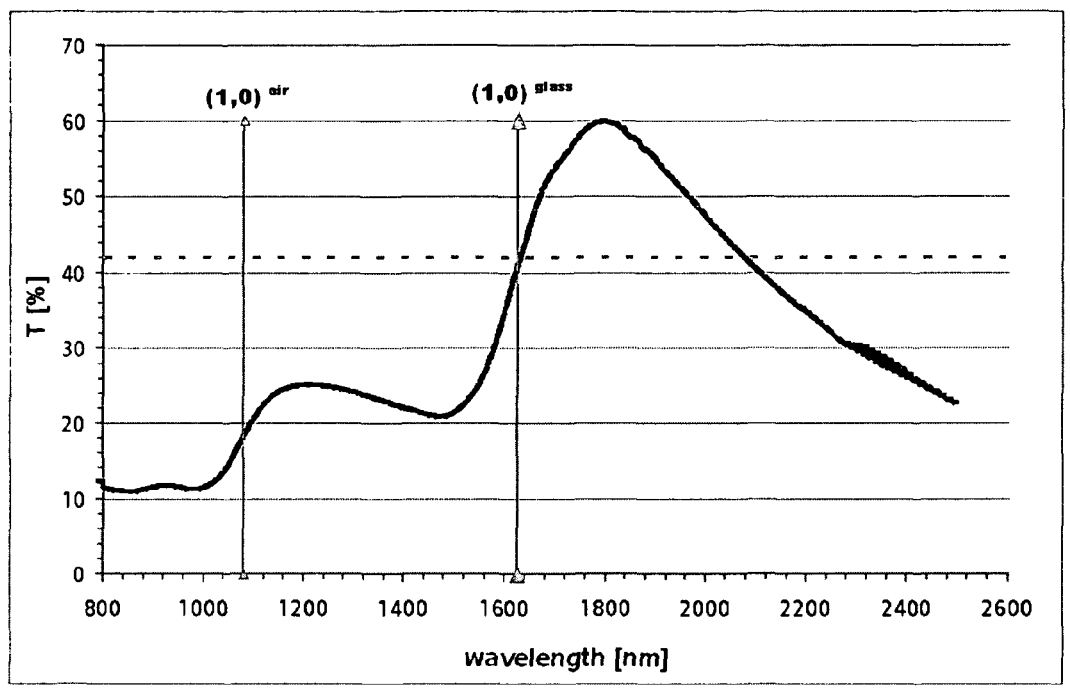
FIG. 3. Spectrum of the obtained hole array in gold films.

In order to demonstrate that the lattice parameters and by this the optical properties can be tuned via the swelling ratio and the diameter of the used microspheres, hexagonal hole arrays in gold films on the basis of three types of polyNIPAM microspheres which differ in their swelling ratio and diameter were produced. Transmission spectra of the obtained structures were measured at normal incidence in an UV-VIS-NIR spectrometer (Cary 5000 (Varian, USA). An exemplary spectrum is shown in FIG. 3 and demonstrates an extraordinary transmission of light ("EOT"). This means that the transmittance is enhanced in comparison to the open area fraction of the nanostructure (grey dotted horizontal line in FIG. 3).

In order to determine the near-range and far-range order of the lithographic masks, the radial distribution functions (RDF) were determined using image analysis.

Figure 6:
FIG. 6. illustration of the near-range order and far-range order in a nanohole array.

The RDF for a perfect periodic lattice is an infinite periodic function, with each oscillation representing a concentric microsphere layer of the lattice relative to the position of the central microsphere (see FIG. 6). The term "near-range order" as used herein refers to the order of the first concentric layer of microspheres surrounding the central microsphere. Consequently, "far-range order" refers to the following concentric layers. For non-perfect lattices, the RDF cannot be infinite periodic. The length scale with which the oscillation of the RDF decays or fades away can be used to indicate the degree of far-range order. The near-range order corresponds to the width of the first oscillation peak. The variance of the distances between the microspheres in the first concentric layer of the lattice and the central microsphere is low if the first oscillation peak shows a narrow shape.

Figure 7A:
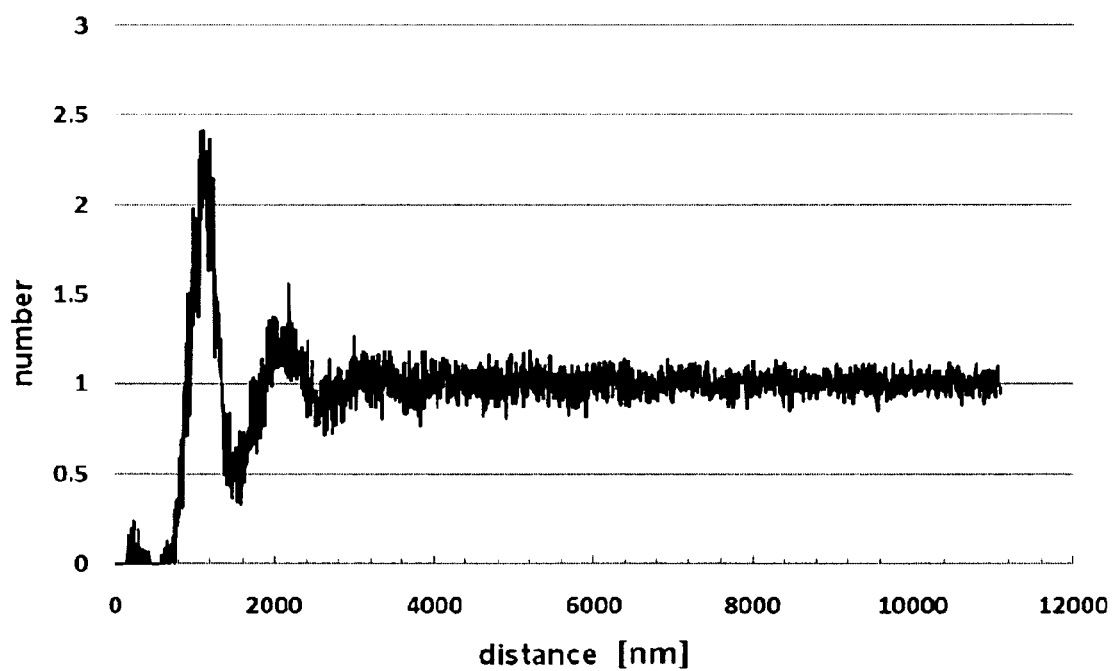
FIG. 7. Radial distribution functions (RDF) of nanoholes produced by different methods.
(A) Radial distribution function obtained with microspheres which had been dropped onto the substrate and air-dried;
(B) Radial distribution function obtained with spin-coating.
Figure 7B:
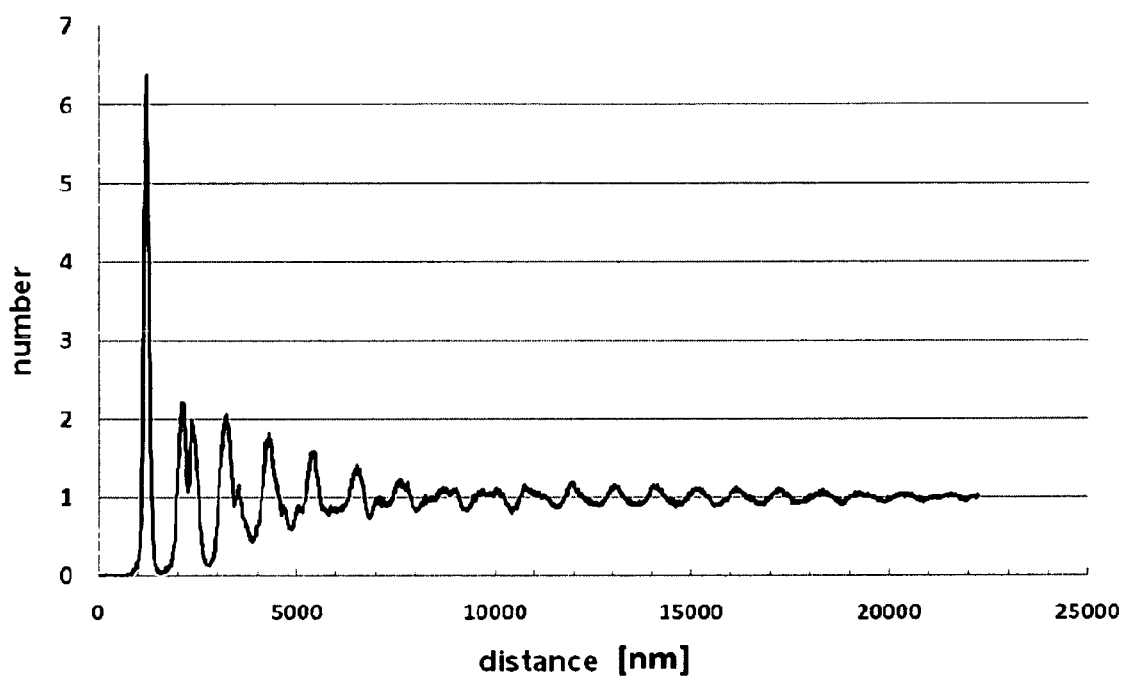

FIG. 7 shows the radial distribution functions (RDF) of nanoholes produced by different methods. Fig. A represents radial distribution function obtained with SP13 microspheres which had been just dropped onto the substrate and air-dried: The RDF shows a broad peak for the first layer of microspheres, indicating a poor near-range order. Moreover, the RDF already decays after the second layer, indicating a poor far-range order as well. FIG. 7B represents the radial distribution function obtained with SP13 microspheres after a spin-coating treatment of the invention. The RDF shows a narrow first peak (high near-range order) and does not completely fade away even beyond 22 µm (maximum of the image analysis).

The most relevant parameters from the image analysis are listed in the following tables.

Analysis of Near-Range Order

| Sample | Mean value of the first peak [nm] | Standard deviation [nm] |
|---|---|---|
| SP13 (direct air-drying) | 1135.25 | 185.783 |
| SP13 (spin-coating) | 1203.9 | 64.35 |
| SP73 (spin-coating) | 622.819 | 35.1199 |
| R13 (spin-coating) | 441.305 | 23.9693 |
| PS-600 nm | 584.357 | 11.6427 |
| PS-600 nm-2 | 585.883 | 15.6044 |

Analysis of Far-Range Order

| Sample | Decay length in lattice layers | Decay length in µm |
|---|---|---|
| SP13 (direct air-drying) | 3 | 3 |
| SP13 (spin-coating) | >20 | >22 |
| SP73 (spin-coating) | 12 | 6.5 |
| R13 (spin-coating) | >11 | >4 |
| PS-600 nm | 12 | 9.2 |
| PS-600 nm-2 | 16 | 8 |

*Decay lengths of > x indicate that the RDF did not completely decay in the observed area of the image. The analysis of larger image areas was not possible for technical reasons.

The analysis of the lattice order demonstrates that the spin-coating method of the invention increases both the near-range order and the far-range order considerably as opposed to a coating method which involves only dropping the polyNIPAM dispersion onto the substrate and subsequent air-drying.

In comparison, arrays of close-packed polystyrene (PS) spheres (PS-600 nm, and PS-600 nm-2) prepared according to a similar method as described by Rybczynski et al., Colloids and Surfaces A 2003, 219, 1-6, showed a slightly better near-range order (presumably due to the more narrow size distribution of the PS spheres in comparison to pure pNIPAM spheres), whereas the far-range order is comparable with that of the spin-coated polyNIPAM microspheres. To provide nanohole arrays, however, these reference arrays of PS microspheres would require a subsequent reactive ion etching step as disclosed in, e.g., Murray et al. (Physical Review B 69, 165407-1-165407-7 (2004) and also involve the corresponding drawbacks as already outlined above (see the back ground section of the present application).

EXAMPLE 3

Testing the Sensing Capability of the Fabricated Hole Arrays

In order to prove the sensing capability of the hole arrays obtained by the present invention, different arrays were produced as outlined above and transmission spectra are measured before and after treatment of the nanostructured surfaces with bovine serum albumin (BSA).

Figure 8:
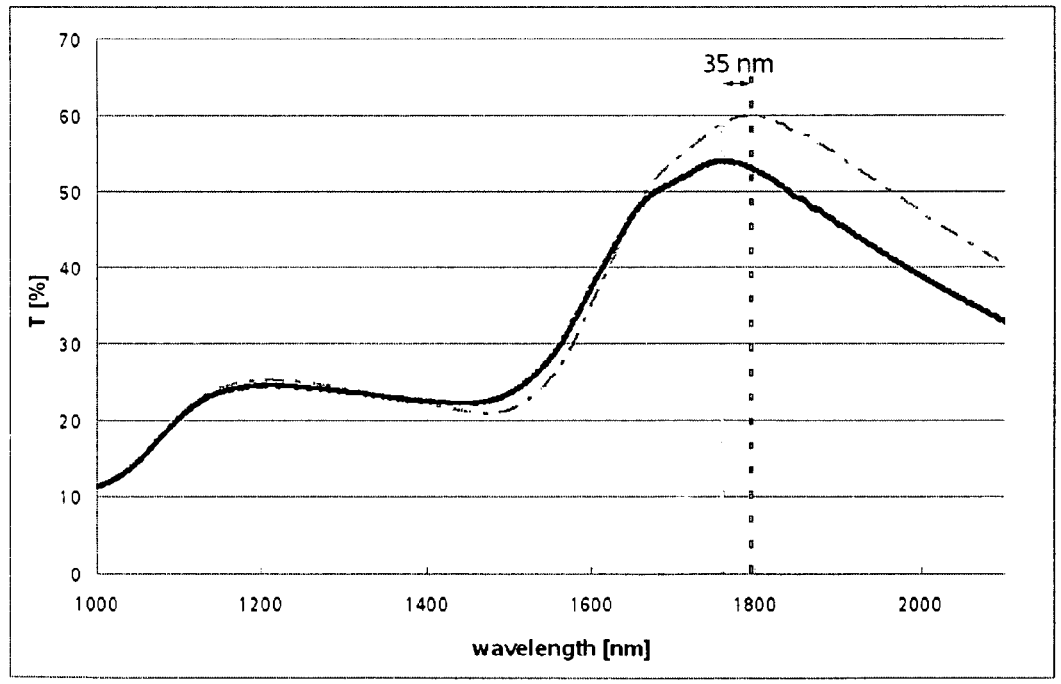
FIG. 8. Spectra of a nanohole array before and after decoration with BSA.

Specifically, nanostructured samples were immersed in 100 μM aqueous solution of BSA and incubated for 5 h. UV-VIS-NIR spectra for a sample before and after binding of BSA are presented in FIG. 8. FIG. 8 shows that the adsorption Of BSA to the surface results in a shift of the (1,0) glass peak by approximately 35 nm to the red.

This result indicates that the prepared hole arrays are capable to detect the adsorption of molecular layers to the sample surface and that the present fabrication method for sub-wavelength hole arrays in metallic films is suitable for the production of sensors with properties comparable to hole arrays prepared by more sophisticated methods such as focused ion beam milling or electron beam writing.

The invention claimed is:

1. A method for producing a highly ordered array of nanoholes in metallic films on a substrate, comprising the steps:
    a) providing microspheres comprising poly-N-isopropylamide (polyNIPAM), the microspheres being selected from pure poly-N-isopropylamide (polyNIPAM) hydrogel microspheres, and polymeric or inorganic beads carrying poly-N-isopropyl-amide (polyNIPAM) hydrogel chains,
    b) spin coating an aqueous dispersion of said microspheres onto a substrate and drying the dispersion, which results in a non-close packed ordered array of the microspheres, wherein the spin coating comprises at least two different spinning operations with different speeds, and a lower alkyl alcohol is added to the aqueous dispersion before the spin coating step,
    c) generating a metallic film on the substrate,
    d) removing the microspheres from the surface of the substrate which results in an ordered array of nanoholes on the substrate, and
    e) optionally increasing the thickness of the metallic film by selective electroless plating.

2. The method according to claim 1, further comprising
    f) incubation of the substrate obtained in step d) or e) in a vacuum oven.

3. The method according to claim 1, wherein the lower alkyl alcohol is a member selected from the group consisting of methanol, ethanol and propanol.

4. The method according to claim 1, wherein the metallic film is a noble metal film.

5. The method according to claim 1, wherein the metallic film in step c) is generated by thermal evaporation.

6. The method according to claim 1, wherein the metallic film in step c) is generated by functionalizing surface areas not covered by microspheres with a compound which enables or favors a selective deposition of a metal on the substrate by electroless plating.

7. The method according to claim 6, wherein the metal is gold and the compound used for functionalizing the surface is an aminosilane.

8. The method according to claim 1, wherein the method used for removing the microspheres in step d) is ultrasonication.

9. The method according to claim 1, wherein the method used for removing the microspheres in step d) is a flame annealing step at a temperature in a range from approximately 400 to 1500° C. which pyrolyzes and removes the polyNIPAM microspheres but does not negatively affect the metallic film.

10. The method according to claim 1, wherein the metallic film is a gold or silver film.

\* \* \* \* \*